United States Patent [19]

Milde et al.

[11] Patent Number: 6,077,479
[45] Date of Patent: *Jun. 20, 2000

[54] APPARATUS FOR THE DISINFECTION OF LIQUIDS

[75] Inventors: Helmut I Milde, Boxford; Sanborn F Philp, Pittsfield, both of Mass.

[73] Assignee: Ion Physics Corporation, Atkinson, N.H.

[*] Notice: This patent issued on a continued prosecution application filed under 37 CFR 1.53(d), and is subject to the twenty year patent term provisions of 35 U.S.C. 154(a)(2).

[21] Appl. No.: 08/983,534

[22] PCT Filed: Jul. 25, 1996

[86] PCT No.: PCT/US96/12176

§ 371 Date: Jan. 7, 1998

§ 102(e) Date: Jan. 7, 1998

[87] PCT Pub. No.: WO97/04858

PCT Pub. Date: Feb. 13, 1997

Related U.S. Application Data

[60] Provisional application No. 60/002,401, Jul. 27, 1995.
[51] Int. Cl.[7] .................................. C25B 9/00; C02F 1/48
[52] U.S. Cl. ........................... 422/23; 204/554; 204/263; 204/666; 204/672; 210/748
[58] Field of Search .......................... 422/22, 23, 186.03, 422/186.04; 204/252, 273, 263, 265, 266, 262, 158.2, 554, 666, 672; 210/748, 243

[56] References Cited

U.S. PATENT DOCUMENTS

| | | | |
|---|---|---|---|
| 4,457,221 | 7/1984 | Geren | 99/451 |
| 5,130,032 | 7/1992 | Sartori | 210/748 |
| 5,338,421 | 8/1994 | Abe et al. | 204/186 |
| 5,575,974 | 11/1996 | Wurzburger et al. | 422/22 |
| 5,690,978 | 11/1997 | Yin et al. | 426/237 |

OTHER PUBLICATIONS

1990 IEEE Industry Applications Meeting M12 90; "Inactivation of Viruses Using Pulsed High Electric Field": Akira Mizuno, et al.; pp. 713–715.

*Primary Examiner*—Elizabeth McKane
*Attorney, Agent, or Firm*—Nields, Lemack & Dingman

[57] ABSTRACT

Apparatus for the destruction of inactivation of microbes by subjecting them to a high potential gradient. The apparatus includes a processing chamber containing spaced apart electrodes, at least one solid insulating barrier dividing the space within the chamber, the barrier having at least one passageway such that no fluid can pass through the chamber without flowing through the passageway, and a voltage source for providing a pulse of voltage.

24 Claims, 5 Drawing Sheets

APPARATUS FOR THE DISINFECTION OF LIQUIDS

This application claims the benefit of U.S. provisional application Ser. No. 60/002/401 filed Jul. 27, 1995.

BACKGROUND OF THE INVENTION

1. Field of the Invention

The invention relates to the destruction or inactivation of microbes by subjecting them to a high potential gradient.

2. Description of the Related Art

As shown by publications in the open technical literature (see Technical Bibliography, below) it has been known for at least fifty years that microbes can be destroyed or deactivated by high potential gradients. In the earliest publications (1949–1965) practical application of this phenomenon for the purpose of disinfecting liquids—and liquid foods in particular—was emphasized. Somewhat later (1970–1985), carefully controlled application of high potential gradients to the manipulation of biological cells was studied and reported. Publications described, inter alia, the use of high potential gradients to render the membranes of biological cells permeable, to organize a number of cells into a group and to accomplish the fusion of two or more cells. Practical devices to accomplish these things were developed and offered for sale as commercial products for use in biological laboratories. The microbiological studies associated with this work provided valuable fundamental information on the effect of high potential gradients on cells. Among other things, it became evident that high potential gradients produce porosity and, in some cases, permanent damage to cell membranes by exerting electromechanical force (electrophoretic force) on the membrane. In other words, the observed effects were due to these forces and not due to electric currents or ohmic heating.

While some microbes—such as spores, in particular,—can be found in gaseous media (in the air, for example) or in solid materials or on the surfaces of solid materials, the vital processes of most microbes require a liquid medium—usually an aqueous medium. Such liquid media are usually weak electrolytes (water being an example) and consequently these media have comparatively high electrical conductivity. Conductivity of 0.05 Siemens (S) per meter is a typical value; but values differing from this by a factor of $10^6$ would still be classified as "semi-conducting", or "non-insulating". Consequently, it was recognized from the earliest work (1949–1960) that high potential gradients could be applied successfully to media containing microbes only under certain special conditions. A potential gradient of $10^6$ volts/meter is of the order of the lowest gradient which will have a permanent effect on a microbe. Such a gradient, applied as a steady (DC) gradient to a medium having a conductivity of 0.05 S/m, would result in a current density of $5 \times 10^4$ amp/m$^2$, with consequent power dissipation of 50,000 Megawatts/m$^3$; and the temperature of the medium would rise at an initial rate of roughly 12,000° C./sec. Of course, these considerations were well-known to all who have worked on this subject. Some of the earliest work applied high-frequency AC voltages (Burton—1949; Doevenspeck—1961) but by 1965, pulsed voltages had become accepted as the preferred means of creating high potential gradients in the various media which were studied. (E.g., Hamilton & Sale—1967; Sale & Hamilton—1967, 1968). Pulse lengths in the range 0.1 microsec to several milliseconds were employed. It was established that the effect of potential gradients on cells—as measured by the induced porosity of the membrane or by the lethal effect on the cells—increased rapidly as the magnitude of the gradient increased. Sale and Hamilton (1968) presented a formula for the potential difference across a microbe in an electric field which has been widely used ever since. They assumed a spherical cell of radius $a_0$ in an electrolytic medium (specific resistance $\rho$ and dielectric constant $\kappa$). The cell membrane is assumed to have a very high resistance—high enough that it can be approximated as a perfectly-insulating membrane—while the interior of the cell is assumed to be conducting; that is, its specific resistance is less than $\rho$. A uniform potential gradient $E_0$ is impressed on the medium containing the cell. Although the cited paper does not give the derivation, it can be shown that the maximum potential difference occurs between the poles of the spherical cell, in the direction of $E_0$. This potential difference, $V_{max}$ is $$V_{max} = 3 a_0 E_0$$

Presumably, this potential would be divided equally between the membranes at either pole. If the membrane has a thickness $\tau$, then the potential gradient $E_p$ at the poles (where this gradient has its maximum value) would be $$E_p = (3/2)(a_0/\tau) E_0$$

Thus, the gradient in the membrane increases with an increase in the overall size (represented by the radius $a_0$) of the cell and decreases with an increase in the membrane thickness.

Below a certain critical gradient—which depends upon the type of cell and is of the order of 10 kV/cm—the porosity induced in the cell membrane is reversible. That is, when the gradient is removed, the membrane regenerates its properties. Whereas, for values of gradient above the critical value, there is an increasing probability that the cell will be destroyed. There is also evidence that—for a given value of potential gradient—the effect increases with increasing time of application.

Various systems for applying high potential gradients to a medium containing microbes are disclosed in U.S. Pat. No. 5,048,404 to Bushnell et al. and in U.S. Pat. No. 5,235,905 to Bushnell et al. Apparatus for inactivation of viruses using pulsed high electric field is disclosed in an article by Mizuno et al. entitled "Inactivation of Viruses using Pulsed High Electric Field" at Conference Record, Annual Meeting, IEEE Industry Applications Society, page 674, 1990.

| Technical Bibliography | |
|---|---|
| 1949 | H. Burton, National Institute for Research in Dairying, Paper #1041, Reading, England |
| 1961 | Doevenspeck, Fleischwirstschaft 13, 986 |
| 1967 | A. J. H. Sale & W. A. Hamilton, Biochimica & Biophysica Acta 148, 781 |
| 1967 | W. A. Hamilton & A. J. H. Sale, Biochimica & Biophysica Acta 148, 789 |
| 1968 | A. J. H. Sale & W. A. Hamilton, Biochimica & Biophysica Acta 163, 37 |
| 1971 | Roland Benz & K. Janko, Biochimica & Biophysics Acta 455, 721 |
| 1973 | J. M. Crowley, Biophysics Journal 13, 711 |
| 1974 | Ulrich Zimmermann, Gunther Pilwat & F. Riemann, Biophysics Journal 14, 881 |
| 1974 | S. H. White, Biophysics Journal 14, 155 |
| 1974 | Ulrich Zimmermann, Gunther Pilwat & F. Riemann, Dielectric Breakdown in Cell Membranes, in: Membrane Transport in Plants, p. 146, Springer, Berlin |
| 1975 | H. G. L. Coster & Ulrich Zimmermann, Biochimica & Biophysica Acta 382, 410 |

-continued

Technical Bibliography

| | |
|---|---|
| 1975 | F. Riemann, Ulrich Zimmermann & Gunther Pilwat, Biochimica & Biophysica Acta 394, 449 |
| 1975 | Gunther Pilwat, Ulrich Zimmermann & F. Riemann, Biochimica & Biophysica Acta 406, 424 |
| 1975 | J. Requena & D. A. Haydon, Biophysics Journal 15, 77 |
| 1976 | Ulrich Zimmermann, Gunther Pilwat, G. Beckers & F. Riemann, Bioelectrochemistry & Bioenergetics 3, 58 |
| 1976 | Roland Benz & P. Läuger, Journal of Membrane Biology 27, 171 |
| 1977 | Ulrich Zimmermann, F. Beckers & H. G. L. Coster, Biochimica & Biophysica Acta 464, 399 |
| 1978 | G. Boheim & Roland Benz, Biochimica & Biophysica Acta 507, 262 |
| 1978 | J. Vienken, E. Jeltsch & Ulrich Zimmermann, Cytobiology 17, 182 |
| 1979 | Roland Benz & Ulrich Zimmermann, Journal of Membrane Bilogy, 48, 181 |
| 1980 | Roland Benz & Ulrich Zimmermann, Biochimica & Biophysica Acta 597, 637 |
| 1980 | Ulrich Zimmermann, J. Vienken & Gunther Pilwat, Bioelectrochemistry & Bioenergetics 7, 553 |
| 1980 | H. Hulsheger & Eberhard Neumann, Radiation & Environmental Biophysics 18, 281 |
| 1980 | Ulrich Zimmermann, Gunther Pilwat, A Péqueux & R. Giles, Journal of Membrane Biology 54, 103 |
| 1981 | Ulrich Zimmermann, Peter Scheurich, Gunther Pilwat & Roland Benz, Angewandte Chemie 93, 332 |
| 1983 | H. Hulsheger, J Potel & Eberhard Neumann, Radiation & Environmental Biophysics 20, 53 |
| 1986 | Akihira Mizuno & Yuji Hori, IEEE Trans. on Indust. Applications 24, 387 |
| 1989 | Eberhard Niemann, A. E. Sowers & C. A. Jordan, Electroporation and Electrofusion in Cell Biology, Plenum Press, N.Y. |
| 1990 | Akihira Mizuno, et al., Conference Record, Ann. Mtg. Industrial Applications Soc., IEEE, p. 713 |
| 1991 | S. Jayaram, G. S. P. Castle & A. Margaritis, Proc. Annual Mtg. Industry Applications Soc., IEEE, p. 674 |
| 1991 | Yoichi Matsumoto, Norio Shioji, Tokuki Satake & Akihiro Sakuma, Ibid., p. 652 |
| 1991 | J. Wilschut & D. Hoekstra, Membrane Fusion, Marcel Dekker N.Y. |

SUMMARY OF THE INVENTION

The fact that microbes can be destroyed or inactivated by subjecting them to a high potential gradient does not lead to a practical process for disinfection unless the apparatus for its implementation incorporates certain features and, in addition thereto, the electrical, mechanical and chemical parameters of the process are appropriate to the particular desired disinfection. The practical apparatus of the invention accomplishes these objectives and constitutes an innovation.

Figure 1:
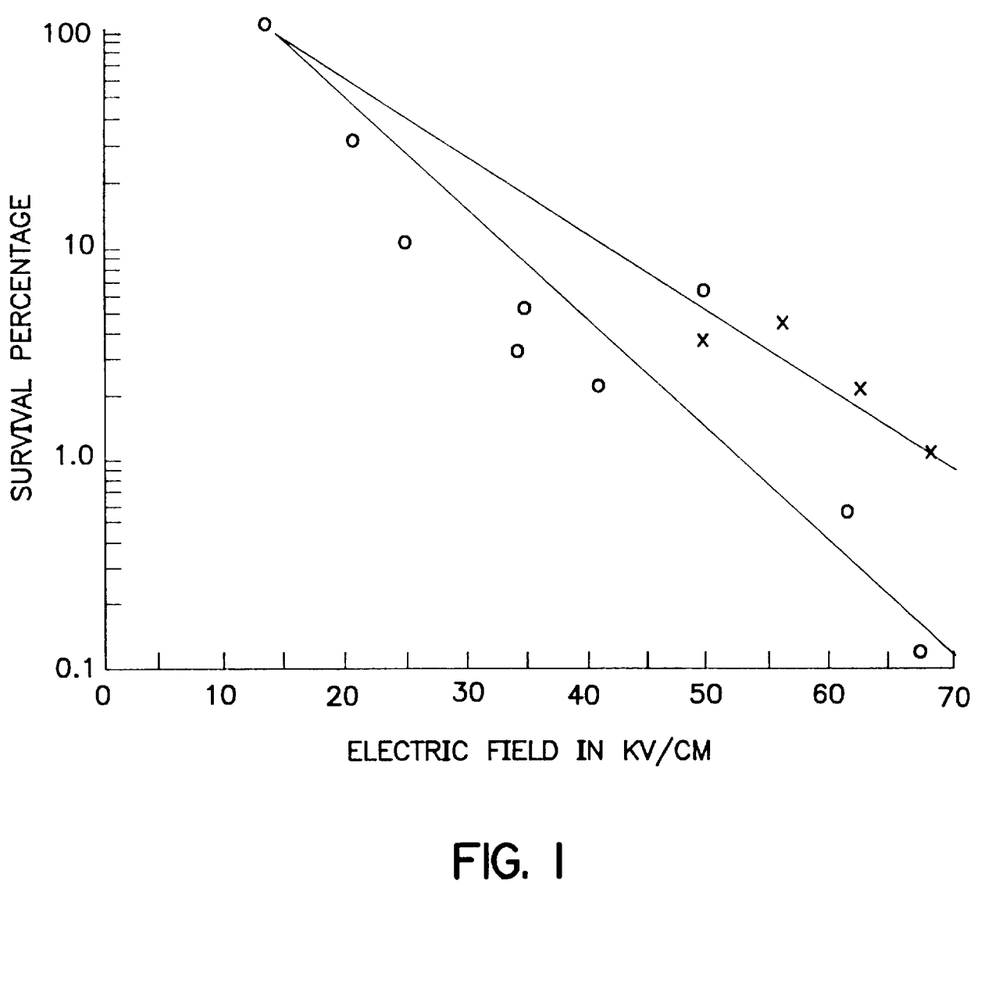
FIG. 1 is a graph showing percentage of bacteria surviving as a function of peak electric field. The solid line applies to fecal coliform bacteria and the broken line to total coliform bacteria counts. (For each experimental point ten pulses were applied.)

The advantages of the invention include the following: (1) The lethal effect of electric fields on microbes increases very rapidly as the strength of the field (i.e., the magnitude of the potential gradient) increases. An example of this is shown in FIG. 1. The subject invention makes it possible to apply very high potential gradients to the electrolytic liquids and partially-conducting liquids in which microbes are found. (2) A practical apparatus must be capable of running reliably for long periods of time without being removed from service for repairs and maintenance work. Typical causes of operating problems are weakening of electrical insulation, which results in electrical discharges, and occasional breakdowns; contamination of electrodes and other internal parts by accumulated debris, and the effect of electrolysis. The subject invention overcomes these reliability problems. (3) The pulsed, high-gradient disinfection technique is not practical if the apparatus and methods employed in its application result in high power consumption. A high power requirement in itself—together with the necessary cooling equipment—would increase the cost of the process and could ultimately make it less advantageous than other alternative processes. The invention herein described is a pulsed, high-gradient apparatus of high efficiency.

As used throughout this specification and claims, the term "liquid" means and includes any conformable substance which can be made to flow through the processing chamber. Thus, the term "liquid" includes, for example, thixatropic fluids and non-newtonian fluids.

BRIEF DESCRIPTION OF THE DRAWINGS

The invention may best be understood from the following detailed description thereof, having reference to the accompanying drawings, in which.

In either FIG. 2 or FIG. 3, $E_1$ is a grounded electrode, $E_2$ is a high voltage electrode and $V_1$, $V_2$ and $V_3$ are fluid volumes at successive places in the flow. Thus, the portions of the boundary of the processing cell through which the liquid enters and leaves are at ground potential; this is an important feature of the invention.

DESCRIPTION OF THE PREFERRED EMBODIMENT

Figure 2:
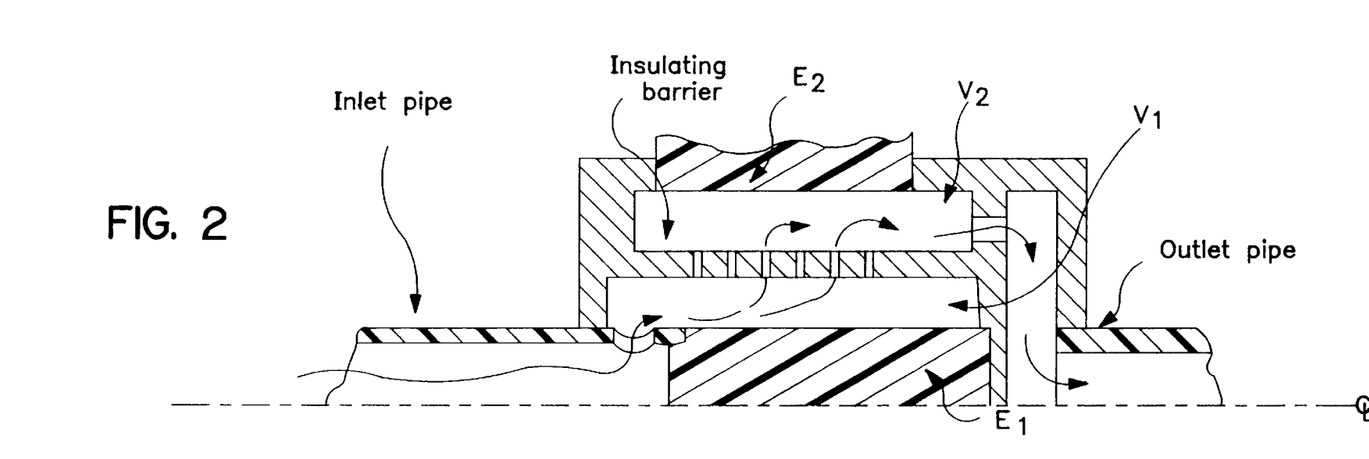
FIG. 2 is an example of the application of an insulating barrier within the processing cell, in which a cylindrical barrier is placed concentrically between cylindrical electrodes.
Figure 3:
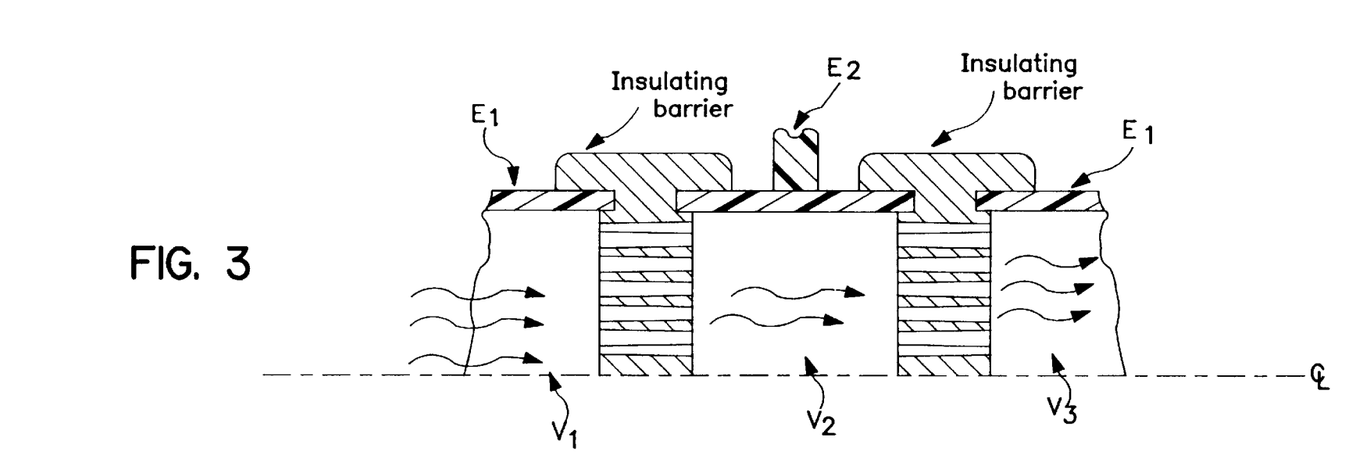
FIG. 3 is another example of the application of an insulating barrier within the processing cell, in which two parallel, insulating barriers are placed perpendicular to the liquid flow. In this embodiment, pairs of grids, of conducting material, could be placed on either side of the insulating barriers, to provide greater control over potential distribution within the processing chamber.
Figure 6:
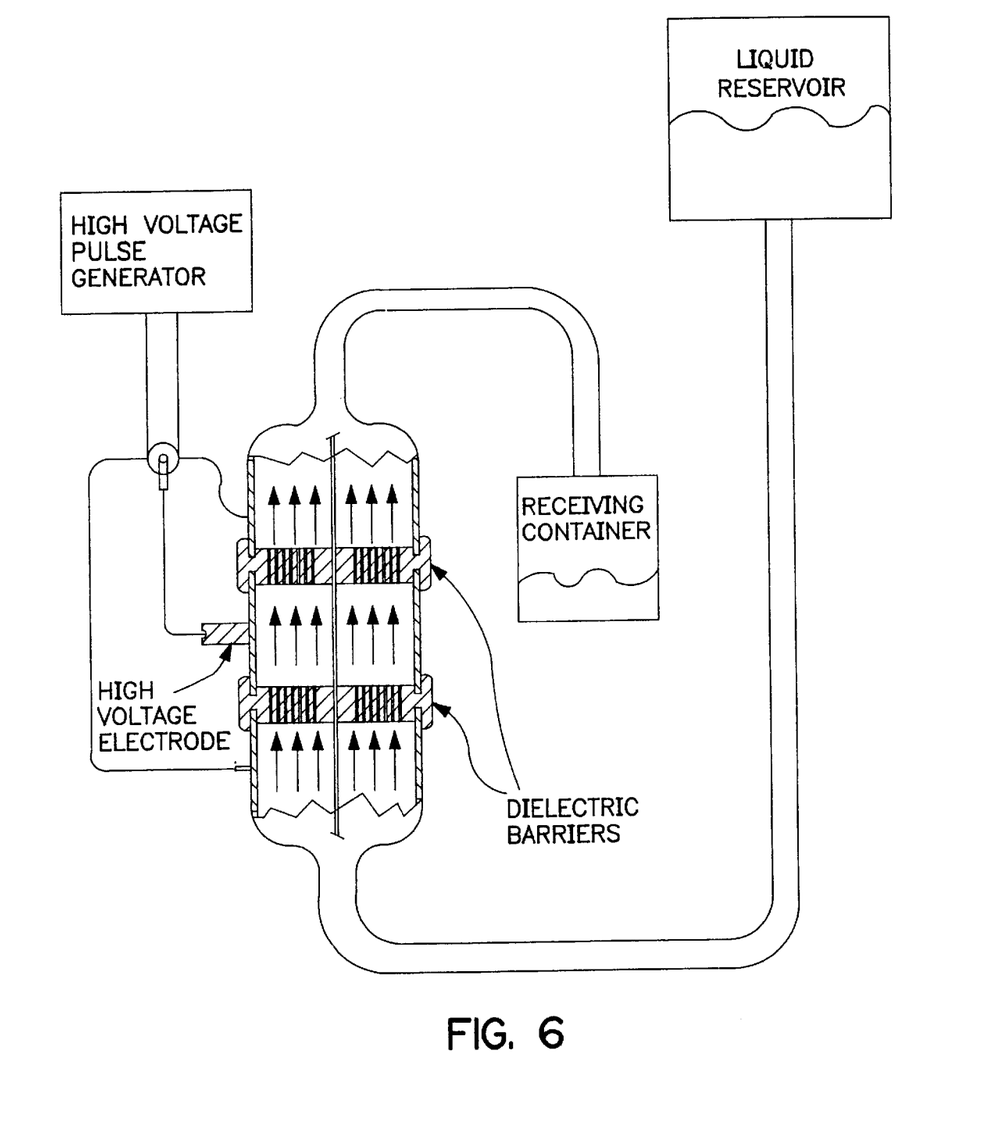
FIG. 6 is a view, similar to that of FIG. 3, and showing the structure in greater detail.

Referring to the drawings, and first to FIGS. 2, 3 and 6 thereof, therein are shown two embodiments of apparatus in accordance with this invention. The features of the invention may be summarized as follows:

1. Use of an insulating barrier within the interelectrode gap.
2. Pulse length.
3. Control of the pulse length and pulse shape by varying the physical and geometrical parameters of the processing chamber.

4. A pulse consisting of a succession of very narrow pulses.
5. Pulses alternating in polarity.
6. Low inductance structure in the assembly of voltage source and processing chamber.
7. A variety of electrode geometries in the processing chamber to meet the requirements of a variety of different microbes in the liquid.
8. Means for excluding gas voids from the processing chamber.
9. Operation of the processing chamber at elevated pressure.

Referring now to each of these features in sequence,

1. Use of an insulating barrier within the interelectrode gap: A solid dielectric is placed within the chamber wherein the flowing liquid is exposed to the pulsed potential gradient. The dielectric, which is pierced with a number of narrow passageways, is so placed within the chamber that it constitutes a barrier to the flow of the liquid. That is, any liquid passing through the chamber must pass through the passageways in the dielectric. Two examples of this use of the dielectric barrier are shown in FIGS. 2 and 3. The path of the liquid being processed is therefore as follows: Through an inlet pipe to a volume $V_1$, through the small passageways in the dielectric barrier into volume $V_2$, and so on, until it reaches the outlet pipe. The passageways have a length equal to or greater than the thickness of the dielectric barrier. These passageways are preferably slots, but may have other geometries, such as that of pin-holes. The transverse section of the slots may have any shape, as long as each passageway has a minor transverse dimension small compared to the thickness of the barrier. The electrical conductivity of the liquid medium, containing the microbes, is very much higher (for example, one million-fold higher) than the conductivity of the dielectric barrier; and the dielectric constant of the liquid is much higher (typically at least 20 times higher) than the dielectric constant of the barrier. Therefore, the gradient which results from a potential difference between $E_1$ and $E_2$ is much higher in the liquid in the passsageways than it is in the liquid in the volumes $V_1$, $V_2$ and $V_3$. The velocity of the fluid should be maintained constant in the passageways. The advantages of this arrangement are: (a) There is a high degree of control over the liquid flow with respect to the regions of the processing chamber which experience the highest potential gradient. In other words, no liquid can pass through the chamber without experiencing the highest potential gradient. (b) The gradient at the electrodes is quite low; and this has at least two advantages: First, this is a situation which is highly favorable to the electrical performance of the apparatus, since electrical breakdown must involve the electrodes, and these are in this case exposed to reduced potential gradients. Second, this means that the current density at the electrodes will be comparatively low and possible accumulation of electrolytic products at the electrode surfaces will be greatly reduced. This idea can be incorporated into a large variety of electrode geometries, of which FIGS. 2 and 3 show two examples.

Figure 4:
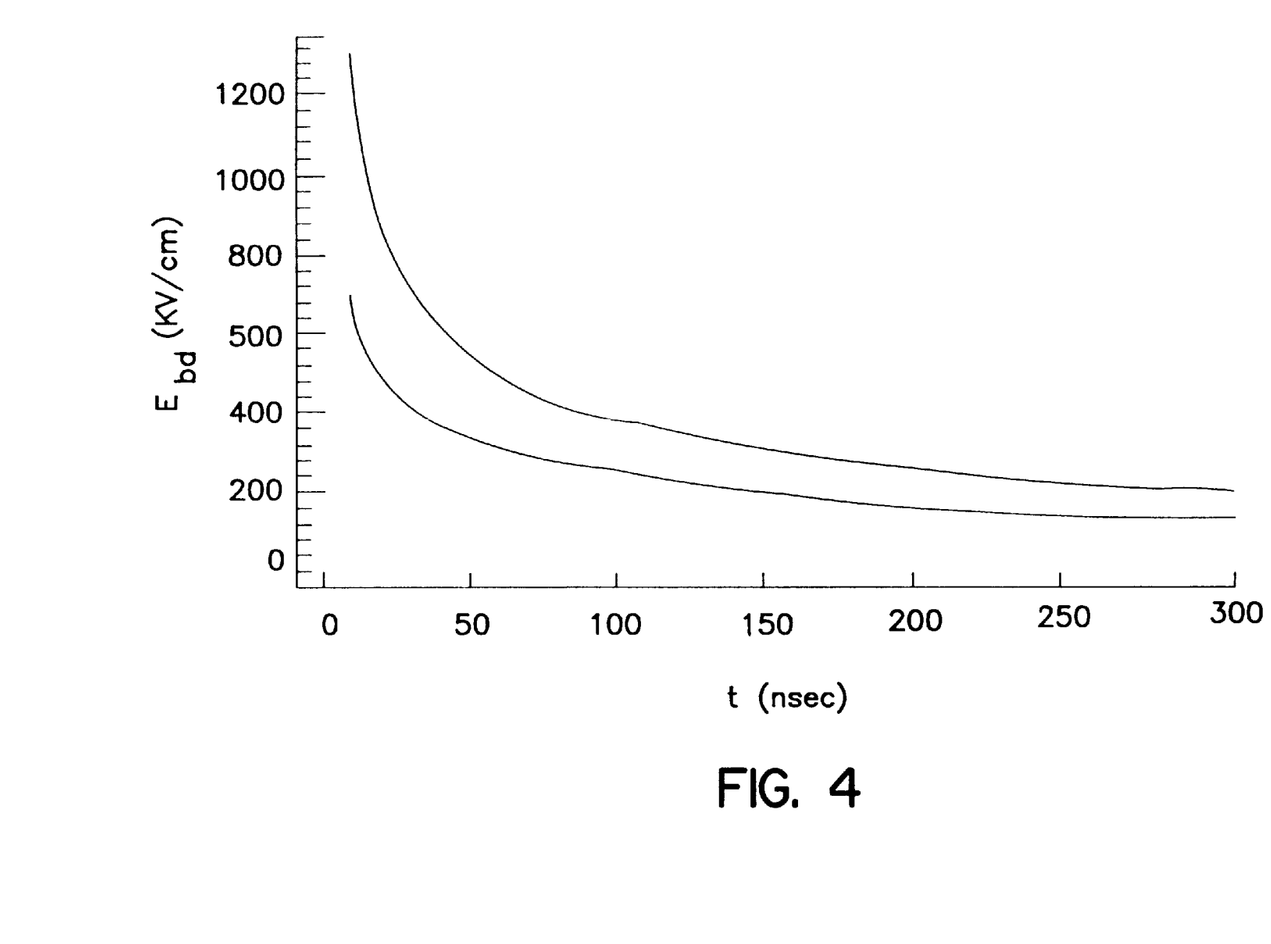
FIG. 4 is a graph showing breakdown potential gradient $E_{bd}$ in water as a function of the length of the applied voltage pulse. In these experiments a sharp-edged electrode faces a plane counter-electrode. The sharp-edged electrode is negative in the case of the upper curve, and it is positive in the case of the lower curve. (From J. Pace VanDevender and T. H. Martin, *Untriggered Water Switching*, Sandia Laboratories Report, 1968.)

2. Pulse length: The maximum gradient which can be supported in a liquid depends on the duration of the gradient, in time. With the maximum, continuous (DC) gradient as a basis, it is found that reducing the time of application permits a higher gradient to be sustained. This increase in gradient with reduction in the time of application is gradual until the time of application becomes very short (of the order of a microsecond). But then for times less than one microsecond the insulating strength begins to rise very rapidly (see FIG. 4). Since the disinfecting effect increases with increasing gradient, the process becomes more effective when very short pulses and the highest possible gradients are employed. This is particularly important when more resistant microbes are to be treated.

3. Control of the pulse length and pulse shape by varying the physical and geometrical parameters of the processing chamber: The arrangement described in (1) ("Use of an insulating barrier within the interelectrode gap") provides a means for controlling the electrical parameters—resistance and capacitance—of the processing cell. This could be accomplished by providing a means for closing and opening—or partly closing and partly opening—the passageways through the dielectric barrier. The pulse shape and pulse length depend—amongst other things—on the resistance and capacitance of the electrical load presented to the source of pulsed voltage. So in this way the pulse characteristics can be modified, as required, without the use of external high-voltage circuit elements connected in parallel with the processing cell, or by modifications to the pulse power supply. Such modifications in pulse shape and pulse length contribute to attaining optimum processing conditions.

4. A pulse consisting of a succession of very narrow pulses: One individual pulse can be formed of a succession (a "train") of very narrow pulses. The train of very narrow pulses may be of decreasing amplitude; and successive pulses may alternate in polarity, as might be the case—for example—in a damped, sinusoidal oscillation. The advantage of this method of operation is that it permits—because of the very narrow individual component pulses—the attainment of a higher potential gradient in the processing chamber.

5. Pulses alternating in polarity: A succession of pulses which alternate in polarity should have the same antimicrobial effectiveness as a succession of pulses, all of the same polarity. However, pulses alternating in polarity would have various advantages, including: (1) Electrolytic effects, in the liquid being processed, would be eliminated or greatly reduced. (2) the circuitry required to generate sharp pulses from an AC input—of the desired frequency—would be simpler than that required for conventional pulse-generating circuits. (The conventional circuits produce mono-polar pulses from a DC input.)

Figure 5:
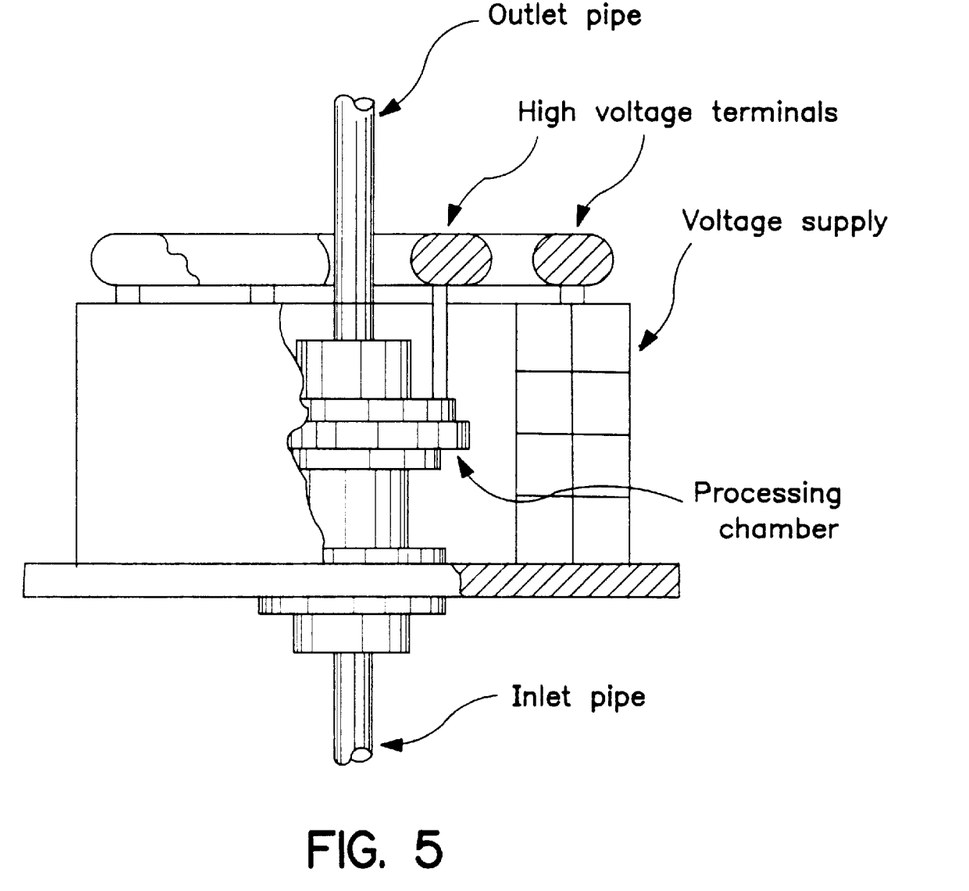
FIG. 5 is an example of a possible arrangement of processing chamber and high-voltage supply which provides low inductance in the voltage supply circuit. In this example, the processing chamber is the inner element in a concentric-cylindrical assembly.

6. Low inductance structure in the assembly of voltage source and processing chamber: Very short, high-voltage pulses imply a high dI/dt (rate-of-change of current with respect to time). This, in turn, puts an upper limit on the permissible inductance in the circuit which connects the voltage source to the processing chamber. Certain arrangements—of which coaxial cylindrical arrangements are an example—permit low inductance connections. An example of a low-inductance assembly of the voltage source and the processing chamber is shown in FIG. 5.

7. A variety of electrode geometries in the processing chamber to meet the requirements of a variety of different microbes in the liquid: Process requirements may differ widely for different microbes. For example, a liquid may be contaminated with cysts which require very high potential gradients for disinfection, but disinfection requirements for these cysts may be met by a surviving fraction of $10^{-3}$. Meanwhile, the same liquid may contain a virus, which is inactivated by a significantly lower value of gradient, but disinfection requirements may be for a surviving fraction of only $10^{-6}$. The very small surviving fraction is achievable only if every bit of the liquid experiences the high gradient. This, in turn, means a uniform-field geometry—such as concentric cylinders, or an arrangement such as that described in (1) hereinabove ("Use of an insulating barrier within the interelectrode gap"). On the other hand, the very high gradients necessary to deal with the cysts are more easily achieved in a non-uniform geometry, such as would be provided by a small-diameter rod surrounded by a concentric-cylindrical opposing electrode or a rod or cylinder surrounded by one or more circular disks, or by any one of—or a combination of—the many configurations which yield non-uniform fields. These electrode arrangements do not subject every bit of the flowing liquid to the same high potential gradient. However, this disadvantage can be overcome to a considerable extent by providing several successive non-uniform field gaps, and also by providing—upstream from the high-voltage gaps—devices which introduce turbulence into the liquid flow. Examples of such devices to excite turbulence are: (a) A sharp lip or edge protruding into the flow. (b) A group of vanes protruding into the flow. (c) A sudden increase in cross-sectional area of the flow. The combination, within the processing chamber, of various electrode geometries providing both uniform and nonuniform fields makes it possible to deal with a variety of disinfection requirements.

8. Means for excluding gas voids from the processing chamber: Included gas in the liquid can lead to corona discharges and breakdown in the liquid. This will result in unreliable operation and—possibly—in undesirable changes in the liquid under treatment. In addition, the dielectric barrier and the associated electrodes may be shaped to minimize the retention of bubbles at any point in the flowing liquid stream. The possibility of included air in the high-gradient regions is reduced if the processing cell is oriented so that it "fills from the bottom". That is, the inlet occurs at the lowest point in the processing chamber and the outlet is at the highest point.

9. Operation of the processing chamber at elevated pressure: Operation of the processing chamber at an elevated pressure may be useful under certain conditions: Except at very low Reynolds' Number, there may be some degree of turbulence in a flowing liquid. For example, around bends, at discontinuities, and so forth. If dissolved gases are present in the liquid, they may form bubbles, under these circumstances, and this could lead to electrical discharges. Operation of the system under a positive pressure will reduce the formation of bubbles under these and other conditions, and lead to a more reliable process. Furthermore, in some cases the microbicidal action of the process may be enhanced by an elevated pressure during processing.

Having thus described the principles of the invention, together with several illustrative embodiments thereof, it is to be understood that, although specific terms are employed, they are used in a generic and descriptive sense, and not for purposes of limitation, the scope of the invention being set forth in the following claims.

What is claimed is:

1. An apparatus for the destruction of microbes, or the deactivation of microbes, present in a liquid, comprising in combination:
    a processing chamber containing electrodes spaced apart by a given distance,
    at least one solid insulating barrier dividing the space within said chamber into at least two volumes,
    said barrier having one or more passageways such that no fluid can pass through said chamber without flowing through said passageway or passageways,
    a voltage source adapted to provide a pulse of voltage such that a voltage gradient effective to destroy said microbes is produced in at least some portion of the space between said electrodes, the gradient in said passageway or passageways being higher than the gradients outside said passageway or passageways,
    wherein each individual voltage pulse has the form of a succession of pulses having the form of a damped sinusoidal oscillation.

2. Apparatus according to claim 1, wherein said success diminish in amplitude.

3. Apparatus according to claim 1, wherein said successive pulses are all of the same polarity.

4. Apparatus according to claim 1, wherein said successive pulses alternate in polarity.

5. Apparatus according to claim 1, wherein the pulses applied are a continuous succession of pulses, uniformly spaced in time, and identical in shape but alternating in polarity.

6. Apparatus according to claim 5, wherein said continuous succession of alternating pulses is generated from an AC input signal having a frequency equal to the desired repetition frequency of the pulses.

7. Apparatus according to claim 1, wherein the processing chamber and the voltage source are connected in a circuit whose electrical inductance is less than 500 nanohenries.

8. Apparatus according to claim 1 including means for controlling or suppressing the formation of bubbles in the liquid.

9. Apparatus according to claim 1, including means for maintaining elevated pressure during the processing of the liquid.

10. Apparatus according to claim 1, wherein said passageways are slots.

11. Apparatus according to claim 1, wherein said chamber has an average electric field, and wherein the electric field near said electrodes is low compared to said average field.

12. Apparatus according to claim 1, wherein said apparatus further comprises an inlet for said liquid and an outlet for said liquid, and wherein said inlet and said outlet are at ground potential.

13. Apparatus according to claim 1, further comprising means transversely arranged to render the electric field more uniform.

14. Apparatus according to claim 1, including means for cooling said liquid.

15. Apparatus according to claim 1 in which the processing chamber is oriented so that an inlet for the flowing liquid is at the lowest point in the chamber and an outlet for the flowing liquid is at the highest point in the chamber.

16. Apparatus according to claim 1, wherein said voltage gradient produced is at least 30 kV/cm.

17. Apparatus for the destruction of microbes, or the deactivation of microbes, present in a liquid, comprising in combination
    at least one processing chamber having electrodes forming two or more interelectrode spaces,
    means for transporting liquid to pulses of high potential gradient caused by pulses of high voltage applied between the electrodes,
    one of said interelectrode spaces providing a substantially uniform potential gradient to all of the interelectrode space through which the liquid flows,
    another of said interelectrode spaces providing at least one region of non-uniform gradient, which therefore varies from a value substantially higher than the average potential gradient to a value less than the average potential gradient.

18. Apparatus according to claim 17, including means for inducing turbulence in said flowing liquid.

19. Apparatus according to claim 17 in which the processing chamber is oriented so that an inlet for the flowing liquid is at the lowest point in the chamber and an outlet for the flowing liquid is at the highest point in the chamber.

20. Apparatus according to claim 17 including means for controlling or suppressing the formation of bubbles in the liquid.

21. Apparatus according to claim 17, including means for maintaining elevated pressure during the processing of the liquid.

22. Apparatus for disinfecting a liquid, comprising:

a chamber containing an inlet, an outlet spaced from said inlet, and first and second spaced apart electrodes;

an insulating barrier between said electrodes defining a first volume between said first electrode and said barrier, a second volume between said second electrode and said barrier, said insulating barrier having one or more apertures therein, said one or more apertures providing the sole means of liquid communication between said first volume and said second volume;

voltage means for creating a pulse of voltage in said chamber, whereby the potential gradient created in said one or more passageways is higher than the potential gradient created in either of said first volume or said second volume; and wherein each individual voltage pulse has the form of a succession of pulses having a damped sinusoidal oscillation.

23. A process for inactivating microbes, comprising:

providing a processing chamber containing electrodes spaced apart by a given distance, at least one solid insulating barrier dividing the space within said chamber into at least two volumes, said barrier having one or more passageways such that no fluid can pass through said chamber without flowing through said passageway or passageways, a voltage source adapted to provide a pulse of voltage such that a voltage gradient effective to inactive said microbes is produced in at least some portion of the space between said electrodes, the gradient in said passageway or passageways being higher than the gradients outside said passageway or passageways, wherein each individual voltage pulse has the form of a succession of pulses;

subjecting said microbes to a potential gradient in said processing chamber; and altering the electrical characteristics in said processing chamber by changing the geometry of said insulating barrier and/or of said passageway or passageways through said insulating barrier.

24. A process according to claim 23, wherein said voltage gradient produced is at least 30 kV/cm.

* * * * *